United States Patent
Sedai et al.

(10) Patent No.: US 11,386,298 B2
(45) Date of Patent: Jul. 12, 2022

(54) UNCERTAINTY GUIDED SEMI-SUPERVISED NEURAL NETWORK TRAINING FOR IMAGE CLASSIFICATION

(71) Applicant: International Business Machines Corporation, Armonk, NY (US)

(72) Inventors: Suman Sedai, Hughesdale (AU); Bhavna Josephine Antony, Brunswick East (AU); Rahil Garnavi, Macleod (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 442 days.

(21) Appl. No.: 16/738,378

(22) Filed: Jan. 9, 2020

(65) Prior Publication Data

US 2021/0216825 A1    Jul. 15, 2021

(51) Int. Cl.
*G06K 9/62* (2022.01)
*G06N 3/08* (2006.01)
(Continued)

(52) U.S. Cl.
CPC .......... *G06K 9/6259* (2013.01); *A61B 3/0025* (2013.01); *A61B 5/004* (2013.01);
(Continued)

(58) Field of Classification Search
CPC .... G06K 9/6259; G06K 9/6268; G06N 20/20; G06N 3/0454; G06N 3/08; A61B 5/0066
See application file for complete search history.

(56) References Cited

U.S. PATENT DOCUMENTS

| 7,937,264 B2 | 5/2011 | Burges et al. |
| 9,317,927 B2 | 4/2016 | Hamarneh et al. |
| (Continued) | | |

FOREIGN PATENT DOCUMENTS

| CN | 110147456 A | 8/2019 |
| CN | 110223281 A | 9/2019 |
| (Continued) | | |

OTHER PUBLICATIONS

Anonymous "Incrementally Learning Sample-Specific Ensemble of Segmentation Techniques in Medical Imaging", IPCOM000244845D, Jan. 21, 2016, pp. 1-6.
(Continued)

*Primary Examiner* — Utpal D Shah
(74) *Attorney, Agent, or Firm* — Cantor Colburn LLP; Joseph Petrokaitis

(57) ABSTRACT

Aspects of the invention include systems and methods that train a teacher neural network using labeled images to obtain a trained teacher neural network, each pixel of each of the labeled images being assigned a label that indicates one of a set of classifications. A method includes providing a set of unlabeled images to the trained teacher neural network to generate a set of soft-labeled images, each pixel of each of the soft-labeled images being assigned a soft label that indicates one of the set of classifications and an uncertainty value associated with the soft label, and training a student neural network with a subset of the labeled images and the set of soft-labeled images to obtain a trained student neural network. Student-labeled images are obtained from unlabeled images using the trained student neural network.

20 Claims, 3 Drawing Sheets

(51) Int. Cl.
*G06N 20/20* (2019.01)
*A61B 5/00* (2006.01)
*A61B 3/00* (2006.01)
*G06N 3/04* (2006.01)

(52) U.S. Cl.
CPC .......... *A61B 5/0066* (2013.01); *G06K 9/6268* (2013.01); *G06N 3/0454* (2013.01); *G06N 3/08* (2013.01); *G06N 20/20* (2019.01)

(56) References Cited

U.S. PATENT DOCUMENTS

| | | | |
|---|---|---|---|
| 9,418,148 | B2 | 8/2016 | Joshi et al. |
| 9,519,868 | B2 | 12/2016 | Criminisi et al. |
| 10,275,690 | B2 | 4/2019 | Chen et al. |
| 10,354,204 | B2 | 7/2019 | Chen et al. |
| 10,643,602 | B2* | 5/2020 | Li ................... G06N 3/084 |
| 10,839,791 | B2* | 11/2020 | Ichikawa ........... G06N 3/084 |
| 2018/0165554 | A1 | 6/2018 | Zhang et al. |
| 2018/0268265 | A1 | 9/2018 | Sohn et al. |
| 2019/0205748 | A1 | 7/2019 | Fukuda et al. |
| 2019/0213273 | A1 | 7/2019 | Vasudevan et al. |
| 2019/0294864 | A1 | 9/2019 | Chabanne et al. |
| 2020/0034702 | A1* | 1/2020 | Fukuda .............. G06N 3/0454 |
| 2020/0034703 | A1* | 1/2020 | Fukuda .................. G06N 3/08 |
| 2020/0110982 | A1* | 4/2020 | Gou ..................... G06N 3/088 |
| 2020/0334538 | A1* | 10/2020 | Meng ................ G06N 3/0454 |
| 2020/0380313 | A1* | 12/2020 | Keshwani ............ G06V 10/82 |
| 2021/0192357 | A1* | 6/2021 | Sinha .................. G06N 3/088 |

FOREIGN PATENT DOCUMENTS

| | | |
|---|---|---|
| CN | 110443815 A | 11/2019 |
| WO | 2011134110 A1 | 11/2011 |

OTHER PUBLICATIONS

Feltenberger et al., "Image Moderation Using Machine Learning", Defensive Publications Series, Dec. 7, 2017, pp. 1-35.

Sedai et al., "Uncertainty guided semi-supervised segmentation of retinal layers in OCT images", Medical Image Computing and Computer Assisted Intervention, vol. 11764, 2019, pp. 1-9.

Siemens et al., "A Multiple Instance Learning Based Self Learning Approach to Reduce Human Effort in Marking Regions of Interest in Imaging Applications", IPCOM000213368D, Dec. 13, 2011, pp. 1-3.

Yu et al., "Uncertainty-aware Self-ensembling Model for Semi-supervised 3D Left Atrium Segmentation", Medical Image Computing and Computer Assisted Intervention, vol. 11765, Jul. 16, 2019, pp. 1-9.

Zhou et al., "Collaborative Learning of Semi-Supervised Segmentation and Classification for Medical Images", IEEE, 2018, pp. 1-10.

International Search Report and Written Opinion for PCT Application No. PCT/IB2021/050012, dated Apr. 9, 2021, pp. 1-11.

* cited by examiner

UNCERTAINTY GUIDED SEMI-SUPERVISED NEURAL NETWORK TRAINING FOR IMAGE CLASSIFICATION

BACKGROUND

The present invention generally relates to image detection using convolutional neural networks, and more specifically, to uncertainty guided semi-supervised neural network training for image classification.

A convolutional neural network is a multi-layered deep learning algorithm. Deep learning is a type of machine learning that identifies features and classifies them. Classifying refers to labelling each pixel of a set of pixels of an image with one among a set of classifications indicating a feature. Deep learning algorithms are well-suited to diagnostics based on medical imaging, for example, which requires the identification and classification of features in the images. Supervised learning refers to a neural network being trained with a training data set that includes ground truth. That is, the correct output corresponding with the input is known. Unsupervised learning refers to training a neural network with only the input.

SUMMARY

Embodiments of the present invention are directed to uncertainty guided semi-supervised neural network training. A non-limiting example computer-implemented method includes training a teacher neural network using labeled images to obtain a trained teacher neural network, each pixel of each of the labeled images being assigned a label that indicates one of a set of classifications. The method also includes providing a set of unlabeled images to the trained teacher neural network to generate a set of soft-labeled images, each pixel of each of the soft-labeled images being assigned a soft label that indicates one of the set of classifications and an uncertainty value associated with the soft label, and training a student neural network with a subset of the labeled images and the set of soft-labeled images to obtain a trained student neural network. Student-labeled images are obtained from unlabeled images using the trained student neural network.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
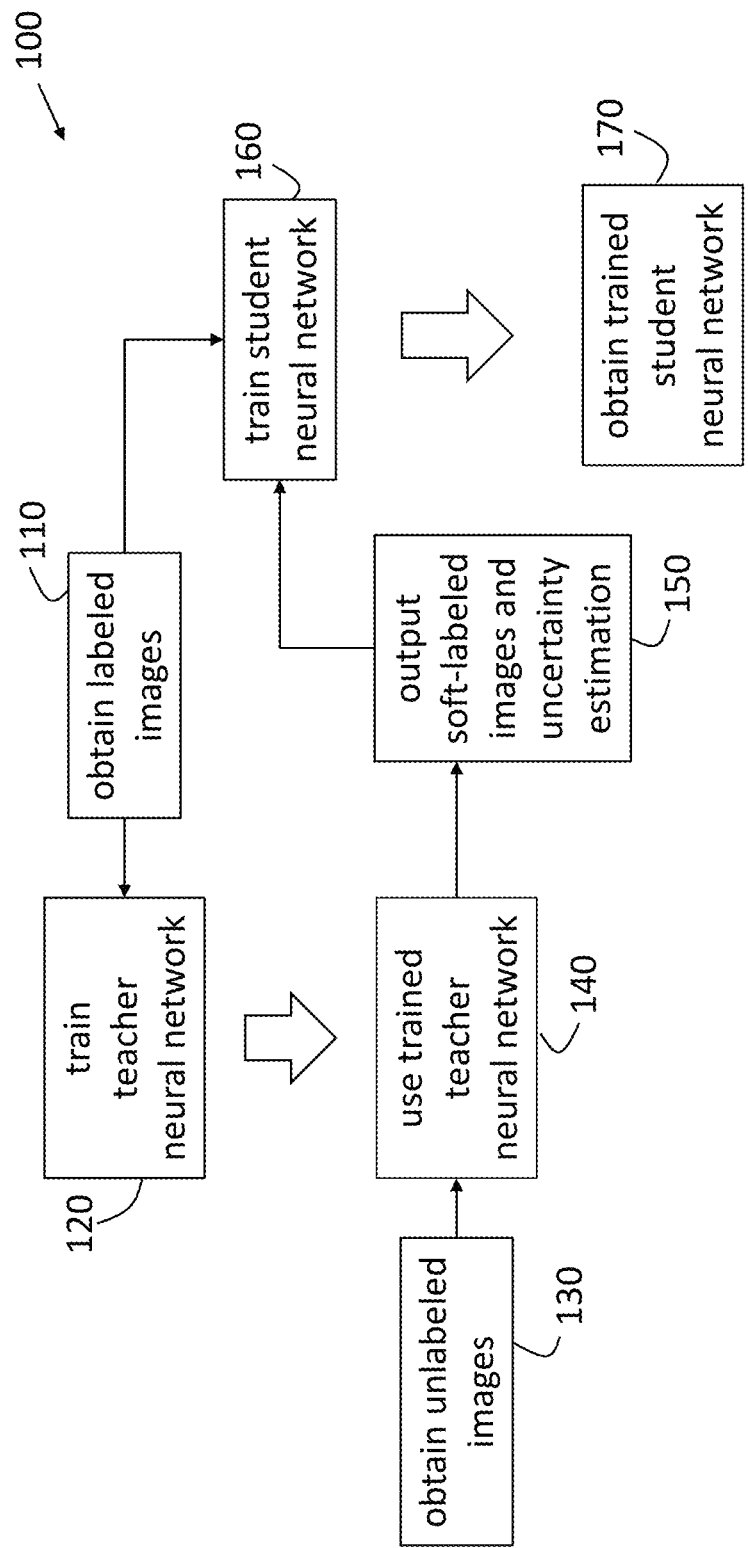
FIG. 1 shows the process flow of a method of performing uncertainty guided semi-supervised neural network training for image classification according to one or more embodiments of the invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

As previously noted, deep learning neural networks can be used to identify features and classify the features in images. These neural networks can be trained to perform medical diagnosis based on the classification of features in medical images, for example. That is, features in the medical images can be identified and labeled with one of a set of classifications. Supervised learning, which involves training the neural network using already labeled images, can produce better results. However, obtaining a sufficiently large training data set for supervised learning can be time-consuming and costly. In the medical diagnosis application, for example, only experts can provide the pixel-wise ground truth annotations of the images needed for supervised learning.

In the typical supervised learning scenario, a neural network is provided with a set of inputs of already-classified images to produce a trained neural network. The larger the set of inputs, the more accurate the resulting trained neural network is likely to be. However, as also previously noted, obtaining a large set of already-classified images can be challenging. In the medical diagnostic application, for example, only experts can determine the labels used to classify the input images.

One or more embodiments of the present invention relate to uncertainty guided semi-supervised neural network training for image classification. As described in greater detail subsequently herein, a teacher neural network undergoes supervised learning using an available set of classified images. The resulting trained teacher neural network then classifies additional images to provide soft labels. Because unclassified images are more readily available than classified images, the soft-labeled images that can be generated from the unclassified images using the trained teacher neural network can be a much larger set than the classified images. The classified and soft-labeled images are then used to train a student neural network. Thus, the student neural network benefits from the larger training data set that results from using both the classified and the soft-labeled images.

In accordance with aspects of the invention, the student neural network benefits from an uncertainty map that indicates a confidence level associated with each label generated by the trained teacher neural network. While optical coherence tomography (OCT) retinal scans are specifically discussed for exemplary purposes, the one or more embodiments of the invention detailed herein apply, as well, to any biomedical or other images with features that may be classified into specific categories. Other exemplary images include magnetic resonance images (MRIs), and other exemplary diagnostics relate to lung nodules and retinal vessels. In the exemplary case of the images being obtained from OCT retinal scans, the fact that the OCT scans measure the thickness of the circumpapillary retinal nerve fiber layer (cpRNFL) and, thus, indicate thinning of the cpRNFL can be used to predict visual functional loss in a patient with glaucoma.

FIG. 1 shows the process flow of a method 100 of performing uncertainty guided semi-supervised neural network training for image classification according to one or more embodiments of the invention. At block 110, a set of labeled images Di is obtained. As previously noted, every pixel of each labeled image is labelled according to a classification that applies to the images. For example, for labeled images Di that are OCT scans, each pixel of each OCT scan can be labelled according to one of eight anatomies of the eye. A teacher neural network is trained with this set of labeled images Di, at block 120, using Bayesian deep learning. The result of the training at block 120 is a trained teacher neural network that can receive an unlabeled image as an input and output soft labels for each pixel of that image, as well as an uncertainty map. The uncertainty map indicates the unreliability of each soft label. The labels output by the trained teacher neural network are referred to as soft labels for explanatory purposes in order to differentiate the output of the trained teacher neural network from the labels in the labeled images Di that are annotated by experts and, thus, represent ground truth.

The processes at blocks 130 through 160 are then performed iteratively in order to obtain the trained student neural network at block 170. These processes are summarized here and further detailed below. The number of iterations can be based on convergence of a validation loss that is determined using a special validation training set at each iteration. At block 130, a subset $\hat{x}_u$ of unlabeled images $D_u$ is obtained. The number of the unlabeled images in the subset $\hat{x}_u$ may be the same for each iteration. At block 140, by using the trained teacher neural network, soft-labeled images and an uncertainty estimate are output at block 150 for the subset $\hat{x}_u$ of the unlabeled images $D_u$. That is, for each unlabeled image in the subset the trained teacher neural network provides a soft label for each pixel and also indicates the unreliability of each soft label. Thus, a vector of soft labels z and a vector of uncertainty estimates (i.e., uncertainty map u) is obtained, at block 150, for each image in the subset Higher values in the uncertainty map u can denote pixels with soft labels that are more likely to be incorrect. These soft labels can then be correspondingly down-weighted in the training of the student neural network, at block 160. At each iteration, the subset $\hat{x}_u$ with soft labels and a subset $\hat{x}_l$ of the labeled images obtained at block 110 are used to train a student neural network at block 160. The process of training the student neural network, at block 160, is detailed with reference to FIG. 2.

Figure 2:
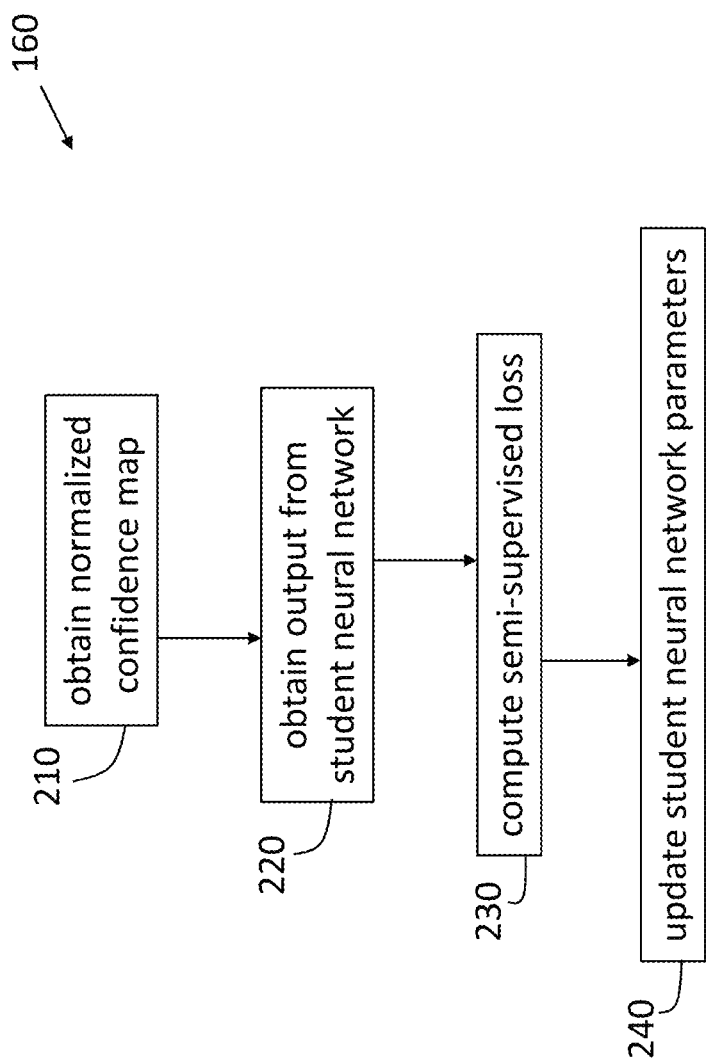
FIG. 2 details the process of training the student neural network by performing uncertainty guided semi-supervised neural network training for image classification according to one or more embodiments of the invention.

FIG. 2 details the process of training the student neural network, at block 160 (FIG. 1), by performing uncertainty guided semi-supervised neural network training for image classification according to one or more embodiments of the invention. The uncertainty guided semi-supervised training refers to the use of the soft labels z and the uncertainty map u provided by the trained teacher neural network at block 150. As previously noted, the uncertainty map u indicates the reliability of the soft label generated by the trained teacher neural network for each pixel of the subset $\hat{x}_u$ and, thus, facilitates weighting of the soft labels in the training of the student neural network.

At block 210, obtaining a normalized confidence map ω refers to converting the uncertainty map u output by the trained teacher neural network according to:

$$\omega = e^{-\alpha u} \quad [\text{EQ. 1}]$$

The positive scalar hyper-parameter a controls the information flow from the trained teacher neural network to the student neural network and, more specifically, controls the use of the soft labels z. That is, if α were set to 0, all of the soft labels z would be weighted equally (i.e., ω=1), but with α>0, a probabilistic selection of more reliable soft labels is made. The normalized confidence map ω∈[0, 1] provides a pixel-wise quality of the soft labels z such that a higher uncertainty value produces a lower quality score (and a lower likelihood that the soft label will be used in training) and a lower uncertainty value produces a higher quality score (and a higher likelihood that the soft label will be used in training). The value of α can be determined empirically. Using the soft labels z of the subset $\hat{x}_u$, obtained from the trained teacher neural network, in addition to the expert-annotated labels of the subset $\hat{x}_l$ of the labeled images increases the training data set used in training the student neural network. In addition, weighting the soft labels z based on uncertainty map u obtained from the trained teacher neural network further improves the training of the student neural network.

At block 220, obtaining output $z_c^t$ from the student neural network refers to using the weighted soft labels and indicates the $t^{th}$ pixel and the $c^{th}$ class. A standard loss $L_{lab}$ is used to denote the loss associated with the subset $\hat{x}_l$ of the labeled images, and the unlabeled loss $L_{unlab}$ associated with the subset $\hat{x}_u$ is formulated as the confidence-weighted cross entropy given by:

$$L_{unlab} = \Sigma_{c=1}^{C} \zeta_c \Sigma_{\forall Z_c} \omega_t \log z_x^t \quad [\text{EQ. 2}]$$

In the exemplary case of the images being OCT scans, the number of classes is 8 (i.e., C=8). $Z_c$ denotes the pixel region of the $c^{th}$ class in the soft label vector z, and $\zeta_c$ is given by:

$$\zeta_c = \begin{cases} 1 / \Sigma_{\forall Z_c} \omega_t, & \text{if } \Sigma_{\forall Z_c} \omega_t > P \\ 0, & \text{otherwise} \end{cases} \quad [\text{EQ. 3}]$$

According to EQ. 3, $\zeta_x = 0$ when the effective number of pixels per class is ≤P. This improves stability of the unlabeled loss when the majority of pixels of $Z_c$ are uncertain. The value of P is set empirically (e.g., P=50 in the exemplary case of the images being OCT scans). The semi-supervised loss $L_{semisup}$ is computed, at block 230, as a sum of the unlabeled loss $L_{unlab}$ and the labeled loss $L_{lab}$ and is given by:

$$L_{semisup} = L_{unlab} + L_{lab} \quad [\text{EQ. 4}]$$

The semi-supervised loss $L_{semisup}$ is used to update the parameters of the student neural network, at block 240, as part of the training process for the iteration.

Obtaining output from the student neural network, at block 220, and computing the semi-supervised loss, at block 230, can be repeated with a particular training data set to determine whether further iterations of the processes at blocks 130 through 160 (FIG. 1) are needed. The particular training data set or validation images include unlabeled images and corresponding labeled images. The above-discussed semi-supervised loss Lsemisup that is computed at block 230 using the image subsets $\hat{x}_u$ and $\hat{x}_l$ is used to update the parameters of the student neural network, at block 240. The semi-supervised loss Lsemisup that is computed at block 230 using the validation images is used to determine convergence. If the semi-supervised loss Lsemisup is converging (e.g., the difference in semi-supervised loss Lsemisup from one iteration to the next is below a threshold value), then the iterations can stop. The iterations of the processes at blocks 130 through 160 can be performed until convergence is achieved or a set number of iterations (e.g., 40,000) is reached.

Figure 3:
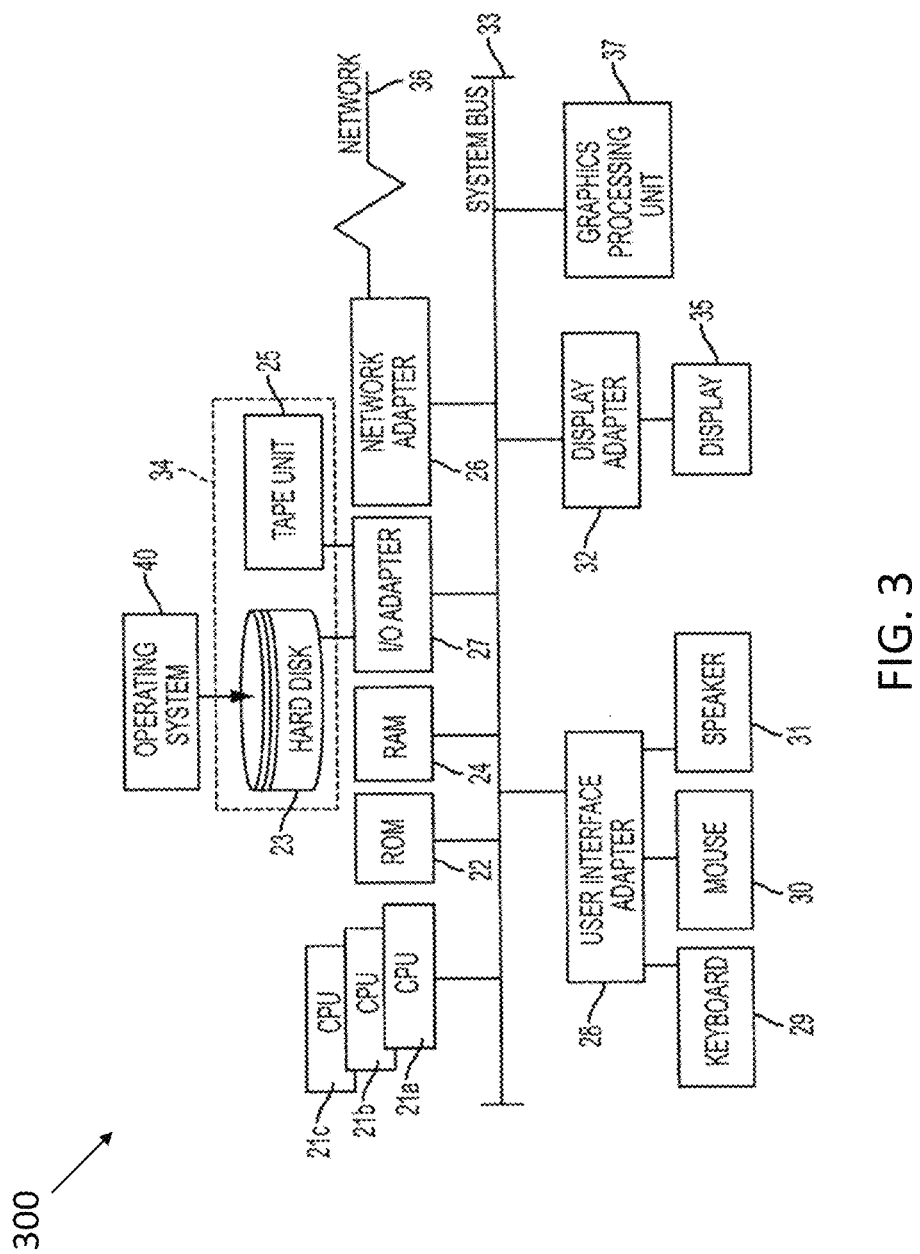
FIG. 3 depicts a block diagram of a processing system for implementing the uncertainty guided semi-supervised neural network training for image classification according to one or more embodiments of the invention.

It is understood that one or more embodiments of the present invention are capable of being implemented in conjunction with any other type of computing environment now known or later developed. For example, FIG. 3 depicts a block diagram of a processing system 300 for implementing the techniques described herein. In the embodiment shown in FIG. 3, processing system 300 has one or more central processing units (processors) 21a, 21b, 21c, etc. (collectively or generically referred to as processor(s) 21 and/or as processing device(s)). According to one or more embodiments of the present invention, each processor 21 can include a reduced instruction set computer (RISC) microprocessor. Processors 21 are coupled to system memory (e.g., random access memory (RAM) 24) and various other components via a system bus 33. Read only memory (ROM) 22 is coupled to system bus 33 and can include a basic input/output system (BIOS), which controls certain basic functions of processing system 300.

Further illustrated are an input/output (I/O) adapter 27 and a communications adapter 26 coupled to system bus 33. I/O adapter 27 can be a small computer system interface (SCSI) adapter that communicates with a hard disk 23 and/or a tape storage drive 25 or any other similar component. I/O adapter 27, hard disk 23, and tape storage device 25 are collectively referred to herein as mass storage 34. Operating system 40 for execution on processing system 300 can be stored in mass storage 34. The RAM 22, ROM 24, and mass storage 34 are examples of memory 19 of the processing system 300. A network adapter 26 interconnects system bus 33 with an outside network 36 enabling the processing system 300 to communicate with other such systems.

A display (e.g., a display monitor) 35 is connected to system bus 33 by display adaptor 32, which can include a graphics adapter to improve the performance of graphics intensive applications and a video controller. According to one or more embodiments of the present invention, adapters 26, 27, and/or 32 can be connected to one or more I/O busses that are connected to system bus 33 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 33 via user interface adapter 28 and display adapter 32. A keyboard 29, mouse 30, and speaker 31 can be interconnected to system bus 33 via user interface adapter 28, which can include, for example, a Super I/O chip integrating multiple device adapters into a single integrated circuit.

According to one or more embodiments of the present invention, processing system 300 includes a graphics processing unit 37. Graphics processing unit 37 is a specialized electronic circuit designed to manipulate and alter memory to accelerate the creation of images in a frame buffer intended for output to a display. In general, graphics processing unit 37 is very efficient at manipulating computer graphics and image processing and has a highly parallel structure that makes it more effective than general-purpose CPUs for algorithms where processing of large blocks of data is done in parallel.

Thus, as configured herein, processing system 300 includes processing capability in the form of processors 21, storage capability including system memory (e.g., RAM 24), and mass storage 34, input means such as keyboard 29 and mouse 30, and output capability including speaker 31 and display 35. According to one or more embodiments of the present invention, a portion of system memory (e.g., RAM 24) and mass storage 34 collectively store an operating system such as the AIX® operating system from IBM Corporation to coordinate the functions of the various components shown in processing system 300.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   training a teacher neural network using labeled images to obtain a trained teacher neural network, each pixel of each of the labeled images being assigned a label that indicates one of a set of classifications;
   providing a set of unlabeled images to the trained teacher neural network to generate a set of soft-labeled images, each pixel of each of the soft-labeled images being assigned a soft label that indicates one of the set of classifications and an uncertainty value associated with the soft label;
   training a student neural network with a subset of the labeled images and the set of soft-labeled images to obtain a trained student neural network; and
   obtaining student-labeled images from unlabeled images using the trained student neural network.

2. The computer-implemented method according to claim 1, further comprising iteratively training the student neural network by providing a different set of unlabeled images to the trained teacher neural network to generate a different set of soft-labeled images and using the different set of soft-labeled images and a different subset of the labeled images in each iteration.

3. The computer-implemented method according to claim 2, further comprising computing a loss value from an output of the student neural network at each iteration, wherein the training the student neural network includes updating parameters of the student neural network at each iteration based on the loss value.

4. The computer-implemented method according to claim 3, wherein the iteratively training the student neural network is performed until convergence of the loss value computed for the student neural network at each iteration is achieved or a predefined number of iterations is reached.

5. The computer-implemented method according to claim 1, further comprising weighting the soft-labeled images generated by the trained teacher neural network based on the uncertainty value associated with the soft label assigned to each pixel.

6. The computer-implemented method according to claim 5, wherein the training the student neural network with the set of soft-labeled images includes excluding soft labels of pixels based on a weight determined according to the weighting.

7. The computer-implemented method according to claim 1, wherein the set of classifications indicates eye anatomies, and the computer-implemented method further comprises diagnosing an eye based on the student-labeled images obtained by inputting optical coherence tomography (OCT) retinal scans as the unlabeled images.

8. A system comprising:
   a memory having computer readable instructions; and
   one or more processors for executing the computer readable instructions, the computer readable instructions controlling the one or more processors to perform operations comprising:
      training a teacher neural network using labeled images to obtain a trained teacher neural network, each pixel of each of the labeled images being assigned a label that indicates one of a set of classifications;
      providing a set of unlabeled images to the trained teacher neural network to generate a set of soft-labeled images, each pixel of each of the soft-labeled images being assigned a soft label that indicates one of the set of classifications and an uncertainty value associated with the soft label;
      training a student neural network with a subset of the labeled images and the set of soft-labeled images to obtain a trained student neural network; and obtaining student-labeled images from unlabeled images using the trained student neural network.

9. The system according to claim 8, wherein the one or more processors further perform iteratively training the student neural network by providing a different set of unlabeled images to the trained teacher neural network to generate a different set of soft-labeled images and using the different set of soft-labeled images and a different subset of the labeled images in each iteration.

10. The system according to claim 9, wherein the one or more processors further perform computing a loss value from an output of the student neural network at each iteration, wherein the training the student neural network includes updating parameters of the student neural network at each iteration based on the loss value.

11. The system according to claim 10, wherein the iteratively training the student neural network is performed until convergence of the loss value computed for the student neural network at each iteration is achieved or a predefined number of iterations is reached.

12. The system according to claim 8, wherein the one or more processors further perform weighting the soft-labeled images generated by the trained teacher neural network based on the uncertainty value associated with the soft label assigned to each pixel.

13. The system according to claim 12, wherein the training the student neural network with the set of soft-labeled images includes excluding soft labels of pixels based on a weight determined according to the weighting.

14. The system according to claim 8, wherein the set of classifications indicates eye anatomies, and the wherein the one or more processors further perform diagnosing an eye based on the student-labeled images obtained by inputting optical coherence tomography (OCT) retinal scans as the unlabeled images.

15. A computer program product comprising a computer readable storage medium having program instructions embodied therewith, the program instructions executable by a processor to cause the processor to perform operations comprising:

training a teacher neural network using labeled images to obtain a trained teacher neural network, each pixel of each of the labeled images being assigned a label that indicates one of a set of classifications;

providing a set of unlabeled images to the trained teacher neural network to generate a set of soft-labeled images, each pixel of each of the soft-labeled images being assigned a soft label that indicates one of the set of classifications and an uncertainty value associated with the soft label;

training a student neural network with a subset of the labeled images and the set of soft-labeled images to obtain a trained student neural network; and obtaining student-labeled images from unlabeled images using the trained student neural network.

16. The computer program product according to claim 15, wherein the operations further comprise iteratively training the student neural network by providing a different set of unlabeled images to the trained teacher neural network to generate a different set of soft-labeled images and using the different set of soft-labeled images and a different subset of the labeled images in each iteration, and computing a loss value from an output of the student neural network at each iteration, wherein the training the student neural network includes updating parameters of the student neural network at each iteration based on the loss value.

17. The computer program product according to claim 16, wherein the iteratively training the student neural network is performed until convergence of the loss value computed for the student neural network at each iteration is achieved or a predefined number of iterations is reached.

18. The computer program product according to claim 15, wherein the operations further comprise weighting the soft-labeled images generated by the trained teacher neural network based on the uncertainty value associated with the soft label assigned to each pixel.

19. The computer program product according to claim 18, wherein the training the student neural network with the set of soft-labeled images includes excluding soft labels of pixels based on a weight determined according to the weighting.

20. The computer program product according to claim 15, wherein the set of classifications indicates eye anatomies, and the computer-implemented method further comprises diagnosing an eye based on the student-labeled images obtained by inputting optical coherence tomography (OCT) retinal scans as the unlabeled images.

* * * * *